United States Patent
Perry

(10) Patent No.: US 8,633,191 B2
(45) Date of Patent: Jan. 21, 2014

(54) ANTI-MICROBIAL AND ANTI-FUNGAL SHAMPOO FOR MAMMALS ESPECIALLY HUMANS AND DOGS

(76) Inventor: Stephen C. Perry, Norwood, MA (US)

(*) Notice: Subject to any disclaimer, the term of this patent is extended or adjusted under 35 U.S.C. 154(b) by 881 days.

(21) Appl. No.: 11/162,612

(22) Filed: Sep. 16, 2005

(65) Prior Publication Data

US 2006/0063777 A1 Mar. 23, 2006

Related U.S. Application Data

(60) Provisional application No. 60/522,367, filed on Sep. 21, 2004.

(51) Int. Cl.
*A01N 43/58* (2006.01)
*A61K 9/00* (2006.01)

(52) U.S. Cl.
USPC .......................................... 514/247; 424/400

(58) Field of Classification Search
USPC ........................................................ 514/247
See application file for complete search history.

(56) References Cited

U.S. PATENT DOCUMENTS

| | | | | |
|---|---|---|---|---|
| 5,181,529 A | * | 1/1993 | Roberts | 132/209 |
| 7,341,983 B2 | * | 3/2008 | Pedersen et al. | 510/383 |
| 2002/0086039 A1 | * | 7/2002 | Lee et al. | 424/401 |

OTHER PUBLICATIONS

Shapiro et al. (Medicated Shampoos; Clinics in Dermatology; vol. 14, Issue 1; Jan.-Feb. 1996; pp. 123-128).*

* cited by examiner

*Primary Examiner* — Layla Soroush
(74) *Attorney, Agent, or Firm* — Malin Haley DiMaggio & Bowen, P.A.

(57) ABSTRACT

A composition for use as a topical treatment for mammals that is both anti-fungal and anti-bacterial, and that is produced preferably in the form of a shampoo. Ketoconazole is the preferred anti-fungal agent used in the composition, and chloroxylenol is the preferred anti-microbial agent.

4 Claims, No Drawings

ANTI-MICROBIAL AND ANTI-FUNGAL SHAMPOO FOR MAMMALS ESPECIALLY HUMANS AND DOGS

CROSS REFERENCE TO RELATED APPLICATIONS

This application claims the benefit of expired U.S. Provisional Patent Application No. 60/522,367 filed Sep. 21, 2004.

FIELD OF THE INVENTION

This invention relates to topical treatment for mammals especially humans and dogs and, specifically, to an anti-fungal and antibacterial shampoo.

DESCRIPTION OF RELATED ART

Mammals, especially humans and dogs, due to their hair structure often experience fungus growth upon their skin and bacteria which can thrive in the environment of hair against the skin. Human and dog skin can be attacked by fungus and bacteria while the hair acts to shield and protect the fungus and the bacteria. One important treatment method is to provide topical treatment to the skin area through the use of a shampoo for cleaning the skin and the hair. While removal of the fungus and bacteria from the skin is important, it is also important to ensure that using agents such as a shampoo do not also do harm to the skin. The purpose of the present invention is to provide a composition that is useful for treating mammals, and especially humans and dogs, as an anti-fungal and antibacterial shampoo using components that will not do harm to the skin of a mammal be it human or dog. The removal and prevention of dandruff, which is a condition that can be caused by certain skin problems, is also important in humans. In many third world countries where the inhabitants do not have access to clean water and often live in conditions that produce fungal and bacterial skin diseases, the present invention can provide a composition for shampoo for third world environments that eliminates prevalent microbial skin diseases. The present invention uses ketoconazole as the preferred fungicide and chlomxylenol as the preferred anti-microbial.

SUMMARY OF THE INVENTION

A composition of matter for treating topically mammals to eliminate fungus and bacteria on the skin, especially in humans and dogs, as a shampoo consisting of water, hydrochloric acid, ketoconazole as a fungicide, methyl glucose dioleate, cocamidopropyl betaine, glyceryl cocoate, olefin sulfonate, lauramine oxide, sodium cocoyl glutamate and hydantoin. Chloroxylenol, the preferred anti-microbial, is also added to the product to prevent bacterial growth, especially in humans and in dogs. The composition can also be produced in the form of a topical anti-fungal agent in a cream, lotion, salve, gel, or bodywash, although a shampoo is the preferred embodiment.

The method of preparing the prescription shampoo, which is also an anti-dandruff shampoo, uses 2% ketoconazole. An over-the-counter shampoo can be prepared using 1.0% ketoconazole. First the pH of a water solution of 4% by weight is adjusted to a pH of 4.0 using urea hydrochloride. The ketoconazole is added to the water with mixing until the mixture is uniform.

In a suitably sized vessel, measure out the second water which is approximately 45.29% of the entire weight of the mixture, PEG-120 methyl glucose dioleate and ketoconazole premix. With a mixing, heat the batch to 85-90° Centigrade. Mix the batch until the mixture is uniform and begin cooling the batch to 70-75° C. with mixing. Add cocamidopropyl betaine, PEG-7 glyceryl cocoate, sodium C14-16 olefin sulfonate, lauramine oxide, and sodium cocoyl glutamate. Mix until uniform. Adjust the pH using citric add to 4.0-4.5. Make certain there is no particulate matter. Cool to room temperature and add the DMDM hydantoin with mixing. The pH at this point should be 4.03. The viscosity according to Brookfield LVT Spindle #3 @ 12 rpm): 1,100 cps.

An object of this invention is to provide an anti-microbial and anti-fungal topical treatment for mammals, especially humans and dogs, that can be used as a shampoo.

Another object of this invention is to provide a shampoo that can be used by humans and dogs or other mammals that is an anti-dandruff shampoo and that does not deleteriously affect the skin of mammals and is both an anti-fungal and antibacterial shampoo.

Still another object of this invention is to treat seborrhea, athlete's foot, jock itch, and ringworm.

The instant invention has been shown and described herein in what is considered to be the most practical and preferred embodiment. The applicant recognizes, however, that departures may be made therefrom within the scope of the invention and that obvious modifications will occur to a person skilled in the art.

DETAILED DESCRIPTION

A composition of matter for producing a topical treatment for mammals that is both anti-fungal and antibacterial and can be used as a shampoo especially for humans and dogs. The composition can also take the form of a topical anti-fungal agent in a cream, lotion, salve, gel, or bodywash, although a shampoo is the preferred embodiment. As shown in Tables 1 and 2 below, there are two formulas for the preferred shampoo that is described below and which uses ketoconazole in two versions. The over-the-counter version for humans would be using 1% by weight ketoconazole while a prescription drug version would use 2% by weight of ketoconazole. Adding chloroxylenol to either the 1% version or the 2% version acts as an antibacterial agent at 0.25-2.0% which is the preferred product for human beings and pets, especially dogs. This can also be used for third world environments where microbial disease is a major issue. Ketoconazole, the preferred anti-fungal agent, and chloroxylenol, the preferred anti-microbial agent, comprise the active ingredients in the composition, while the remaining chemicals, listed below, are detergents, a preservative, and pH balancers used to create the shampoo. These inactive ingredients, including urea hydrochloride, were chosen because of their particular ability to keep the active ingredients, ketoconazole and chloroxylenol, in solution. Urea hydrochloride is a pH-balancing, nitrogen acid salt that has been determined through testing to be extremely effective at dissolving ketoconazole into solution.

In addition to solubilizing the ketoconazole, urea hydrochloride also reduces any skin irritation that the ketoconazole may cause. Moreover, urea hydrochloride also penetrates the skin and enhances the amount of ketoconazole that is retained in the hair and on the skin.

TABLE 1

Example 1, Anti-Dandruff Shampoo with 2% Ketoconazole

| Material | Percent by Weight |
| --- | --- |
| Water | 4.00 |
| Ketoconazole | 2.00 |
| Urea Hydrochloride | q.s. |
| Water | 45.29 |
| PEG-120 Methyl Glucose Dioleate | 1.95 |
| Cocamidopropyl Betaine | 24.40 |
| PEG-7 Glyceryl Cocoate | 4.88 |
| Sodium C14–16 Olefin Sulfonate | 9.76 |
| Lauramine Oxide | 4.88 |
| Sodium Cocoyl Glutamate | 2.44 |
| DMDM Hydantoin | 0.40 |
|  | 100.00% |

Prepare urea hydrochloride by adding prilled urea (35 parts) slowly with mixing and at room temperature to muriatic add (65 parts of 20 degree baume (31.45% minimum and 32.5% average by weight)). The urea hydrochloride effectively dissolves the ketoconazole into solution. Adjust pH of first water to approximately pH 4.0 using a sufficient amount of the urea hydrochloride. Add the ketoconazole to the water with mixing. Mix until uniform.

In a suitably sized vessel, measure out the second water, PEG-120 methyl glucose dioleate and ketoconazole premix. With a mixing, heat the batch to 85-90° C. Mix until batch is uniform. Begin cooling batch to 70-75° C. with mixing. Add cocamidopropyl betaine, PEG-7 glyceryl cocoate, sodium C14-16 olefin sulfonate, lauramine oxide, and sodium cocoyl glutamate. Mix until uniform. Adjust pH using citric add to 4.0-4.5. Make certain there is no particulate matter. Cool to room temperature and add the DMDM hydantoin with mixing.

pH: 4.03

Viscosity (Brookfield LVG Spindle #3 @ 12 rpm): 1,100 cps

TABLE 2

Example 2, Anti-Dandruff Shampoo with 1% Ketoconazole

| Material | Percent by Weight |
| --- | --- |
| Water | 2.00 |
| Ketoconazole | 1.00 |
| Urea Hydrochloride | q.s. |
| Water | 48.29 |
| PEG-120 Methyl Glucose Dioleate | 1.95 |
| Cocamidopropyl Betaine | 24.40 |
| PEG-7 Glyceryl Cocoate | 4.88 |
| Sodium C14–16 Olefin Sulfonate | 9.76 |
| Lauramine Oxide | 4.88 |
| Sodium Cocoyl Glutamate | 2.44 |
| DMDM Hydantoin | 0.40 |
|  | 100.00% |

Prepare urea hydrochloride by adding prilled urea (35 parts) slowly with mixing and at room temperature to muriatic acid (65 parts of 20 degree baume (31.45% minimum and 32.5% average by weight)). The urea hydrochloride effectively dissolves the ketoconazole into solution. Adjust pH of first water to approximately pH 4.0 using a sufficient amount of the urea hydrochloride. Add the ketoconazole to the water with mixing. Mix until uniform.

In a suitably sized vessel, measure out the second water, PEG-120 methyl glucose dioleate and ketoconazole premix. With a mixing, heat the batch to 85-90° C. Mix until batch is uniform. Begin cooling batch to 70-75° C. with mixing. Add cocamidopropyl betaine, PEG-7 glyceryl cocoate, sodium C14-16 olefin sulfonate, lauramine oxide, and sodium cocoyl glutamate. Mix until uniform. Adjust pH using citric acid to 4.0-4.5. Make certain there is no particulate matter. Cool to room temperature and add the DMDM hydantoin with mixing.

pH: 4.03

Viscosity (Brookfield LVG Spindle #3 @ 6 rpm): 1,100 cps

Urea hydrochloride is the preferred pH balancer for most effectively dissolving ketoconazole, however, 0.1 N hydrochloric acid can also be used. In other embodiments of the invention, a blend of urea and any organic or inorganic add, which, when mixed with urea, is safe for use as a topical treatment for mammals, may be used as a pH balancer for the composition to dissolve ketoconazole into solution.

Although ketoconazole is the preferred fungicide, and chloroxylenol is an anti-microbial agent which is preferred, the following can also be used as fungicides in combination with or in place of ketoconazole: amphotericin B, amorolfine, anidulafungin, butenafine, butoconazole, candidin, carbolfuchsin, caspofungin, cidopirox, clotrimazole, dapsone, econazole, emlkonazole, fluconazole, flucytosine, gentian violet, griseofulvin, haloprogin, itraconazole, mafenide, micafungin, miconazole, naftifine, nystatin, oxiconazole, pimaricin, posaconazole, ravoconazole, rimocidin, silver sulfadiazine, sulconazole, terbinafine, terconazole, tioconazole, tolnaftate, undecylenic add, vaddin A or voriconazole.

Also, the following could be used as anti-microbials in lieu of, or in addition to, chloroxylenol: triclosan, alcohol, polyalcohols, hydrogen peroxide, chlorine dioxide and triclocarban.

Using the present invention for humans, dogs and other mammals, this composition and method of making is both an anti-fungal and antibacterial and can prevent dandruff. The invention can also be used to treat seborrhea, athlete's foot, jock itch, and ringworm.

What is claimed is:

1. A composition for topical treatment of mammals that is both anti-fungal and anti-bacterial comprising:
   2.00% ketoconazole;
   4.00% water (first water);
   a sufficient quantity of urea hydrochloride to dissolve the ketoconazole;
   0.25-2.00% chloroxylenol; approximately 45.29% water (second water) added to the composition, wherein the percentage by weight of the second water used to create the composition is reduced according to the amount of chloroxylenol added;
   1.95% PEG-120 methyl glucose dioleate;
   24.40% cocamidopropyl betaine;
   4.88% PEG-7 glyceryl cocoate;
   9.76% sodium C14-16 olefin sulfonate;
   4.88% lauramine oxide;
   2.44% sodium cocoyl glutamate; and
   0.40% DMDM hydantoin.

2. The composition of claim 1, wherein the urea hydrochloride is prepared by adding prilled urea (35 parts) slowly with mixing and at room temperature to muriatic acid (65 parts of 20 degree baume (31.45% minimum and 32.5% average by weight)) to form urea hydrochloride, which effectively dissolves the ketoconazole.

3. A method for producing a composition for topical treatment of mammals that is both anti-fungal and anti-bacterial, said method comprising the following steps:
   adjust the pH of 4.00% volume of water (first water) to approximately pH 4.0 using urea hydrochloride;

add 2.00% ketoconazole to said first water while mixing until uniform to form a ketoconazole premix;

in a vessel, measure out: approximately 45.29% water (second water); 1.95% peg-120 methyl glucose dioleate; and the said ketoconazole premix;

heat the mixture to 85-90° C. while mixing until the composition is uniform;

cool the composition to 70-75° C. while mixing;

add 24.40% cocamidopropyl betaine; 4.88% PEG-7 glyceryl cocoate; 9.76% sodium C14-16 olefin sulfonate; 4.88% lauramine oxide; 2.44% sodium cocoyl glutamate; and mix until uniform;

adjust pH using citric acid to pH 4.0-4.5;

observe to make certain there is no particulate matter within the composition; and cool to room temperature and add 0.40% DMDM hydantoin with mixing add 0.25-2.00% of an antimicrobial agent, chloroxylenol, wherein the percentage by weight of the said second water used to create the composition is reduced according to the amount of said chloroxylenol added.

4. The method of claim 3, wherein the urea hydrochloride is prepared by adding prilled urea (35 parts) slowly with mixing and at room temperature to muriatic acid (65 parts of 20 degree baume (31.45% minimum and 32.5% average by weight)) to form urea hydrochloride, which effectively dissolves the ketoconazole.

* * * * *